United States Patent
Wimmer (10) Patent No.: US 6,575,181 B1
(45) Date of Patent: Jun. 10, 2003

(54) PROBE WASH VESSEL HAVING REMOVABLE INNER CANNULA

(75) Inventor: Gregory A. Wimmer, Perkasie, PA (US)

(73) Assignee: Merck & Co., Inc., Rahway, NJ (US)

( * ) Notice: Subject to any disclaimer, the term of this patent is extended or adjusted under 35 U.S.C. 154(b) by 101 days.

(21) Appl. No.: 09/695,015

(22) Filed: Oct. 24, 2000

Related U.S. Application Data (60) Provisional application No. 60/161,742, filed on Oct. 25, 1999.

(51) Int. Cl.[7] ................................................. B08B 9/00
(52) U.S. Cl. ................ 134/182; 134/166 R; 73/864.22; 422/99; 422/100
(58) Field of Search ....................... 73/864.22; 134/154, 134/155, 170, 182, 183, 186, 166 R, 169 R; 422/63, 64, 99, 100

(56) References Cited

U.S. PATENT DOCUMENTS

| | | | |
|---|---|---|---|
| 4,367,646 A | | 1/1983 | Allen et al. |
| 4,730,631 A | | 3/1988 | Schwartz |
| 4,817,443 A | | 4/1989 | Champseix et al. |
| 4,989,623 A | | 2/1991 | Hoffman et al. |
| 5,133,373 A | * | 7/1992 | Hoffman et al. ............ 134/170 |
| 5,186,194 A | | 2/1993 | Kitajima |
| 5,195,534 A | | 3/1993 | Sarrine |
| 5,279,794 A | * | 1/1994 | Sasao .......................... 134/140 |
| 5,603,342 A | * | 2/1997 | Shambaugh ................. 134/154 |
| 5,725,832 A | | 3/1998 | Gundelsheimer |
| 5,827,744 A | * | 10/1998 | Fose et al. .................... 134/170 |
| 6,422,248 B1 | * | 7/2002 | Furst et al. ................... 134/170 |

FOREIGN PATENT DOCUMENTS

| | | | |
|---|---|---|---|
| EP | 0 290 006 A2 | | 11/1988 |
| EP | 0472213 A2 | * | 8/1991 |
| EP | 0725279 A1 | * | 1/1996 |
| JP | 04105066 A | * | 4/1992 |

* cited by examiner

Primary Examiner—Randy Gulakowski
Assistant Examiner—Joseph Perrin
(74) Attorney, Agent, or Firm—James M. Hunter, Jr.; Mark R. Daniel (57) ABSTRACT

A probe wash vessel characterized as having a cylindrical-shaped, outer test tube with at least two vertically aligned faucets, and an inner cannula positioned within the test tube, wherein the inner cannula is characterized by a top funnel opening attached to a stem, the stem characterized as having two arm extensions are attached to the two faucets, wherein washing fluid influent and effluent through the arm extensions washes a probe inserted through the top funnel into the stem.

12 Claims, 6 Drawing Sheets

PROBE WASH VESSEL HAVING REMOVABLE INNER CANNULA

RELATED U.S. APPLICATION

This application claims the benefit of U.S. application Ser. No. 60/161,742 filed on Oct. 25, 1999.

BACKGROUND OF THE INVENTION

It is well known in the art that probes are used in performing assays which may deal with biological fluids, environmental samples or metal analysis. Such assays generally involve using the probes to draw and dispense either reagents or test samples. Since these probes are used repeatedly to aspirate and dispense a variety of samples or other fluids, they must be washed after each sampling or before each change of reagent in order to prevent the carryover of one fluid to the next and which could contaminate the testing. Before delivering the reaction components to a cuvette, buffer solution is normally passed through the probe to eliminate any residual reaction components prior to subsequent tests. Typically, the wash solution is passed through the probe and dispensed to a remotely positioned waste container. While this internal cleansing of the probe is generally satisfactory, it does not provide for washing of the outer surface of the probe which can retain residual samples in certain assays.

Sample material retained on the probe surface is especially troublesome in automated analyzers where failure to adequately wash the outer surface of the dispensing probe can cause undesired sample carryover to subsequent tests. Preventing sample carryover can be crucial in some assays to maintain the integrity of the sample or the assay.

It is accordingly an object of the present invention to provide a probe wash vessel which has a decreased volume capacity that reduces the chance of carry over contamination and reduces the required wash time.

An additional object of the present invention is to provide a probe wash vessel which is more efficient and allows for more frequent solvent changes.

It is also an object of the present invention to provide a probe wash vessel that can be used with automated equipment, such as an automated sampling device.

SUMMARY OF INVENTION

The present invention relates to a probe wash vessel comprising a) an outer test tube of a first length, having an open top end of a first diameter, a closed bottom end, a first cylindrical sidewall, an interior environment and an exterior environment, said first cylindrical sidewall having an inner surface and an outer surface, which extend between said open top end and said closed bottom end, and at least two holes in said first cylindrical sidewall;

b) at least two faucets, which are aligned with said holes of said outer test tube and attached to the outer surface of said first cylindrical sidewall, one faucet, a lower faucet, being positioned closer to said closed bottom end of said outer test tube and one faucet, an upper faucet, being positioned closer to said open top end of said outer test tube;

c) an inner cannula of a second length which is shorter than said first length, said inner cannula having a top funnel opening, a bottom end, an inner environment, an outer environment and a stem, which comprises a second cylindrical sidewall extending between said top funnel opening and said bottom end, said stem having an outer surface, an inner surface and a second diameter that is smaller than said first diameter, said stem having at least two arm extensions protruding from the outer surface of said stem to allow materials to pass from said inner environment of said inner cannula to said outer environment; and d) said inner cannula being positioned within said interior environment of said outer test tube so that said bottom end and an arm extension of said inner cannula are aligned with said lower faucet of said outer test tube, said top funnel opening fitting securely within said open top end of said outer test tube and said arm extension being aligned with said upper faucet of said outer test tube, to allow materials to be poured into said funnel opening of said cannula and pass through said arm extensions, bottom end and upper or lower faucets to said exterior environment of said outer test tube without being exposed to said interior environment of said outer test tube.

Other objects and advantages of the present invention will become readily apparent to those skilled in this art from the following detailed description, wherein only the preferred embodiment of the invention has been shown, simply by way of illustration of the best mode contemplated. As will be realized, the invention is capable of modifications in various aspects, all without departing from the invention. Accordingly, the drawings and description are to be regarded as illustrative in nature, and not as restrictive.

BRIEF DESCRIPTION OF THE DRAWINGS

The present invention may be described with greater clarity and specifically with reference to the drawings, in which.

DETAILED DESCRIPTION OF THE INVENTION

The present invention relates to a probe wash vessel comprising a) an outer test tube of a first length, having an open top end of a first diameter, a closed bottom end, a first cylindrical sidewall, an interior environment and an exterior environment, said first cylindrical sidewall having an inner surface and an outer surface, which extend between said open top end and said closed bottom end, and at least two holes in said first cylindrical sidewall;

b) at least two faucets, which are aligned with said holes of said outer test tube and attached to the outer surface of said first cylindrical sidewall, one faucet, a lower faucet, being positioned closer to said closed bottom end of said outer test tube and one faucet, an upper faucet, being positioned closer to said open top end of said outer test tube;

c) an inner cannula of a second length which is shorter than said first length, said inner cannula having a top funnel opening, a bottom end, an inner environment, an outer environment and a stem, which comprises a second cylindrical sidewall extending between said top funnel opening and said bottom end, said stem having an outer surface, an inner surface and a second diameter that is smaller than said first diameter, said stem having at least two arm extensions protruding from the outer surface of said stem to allow materials to pass from said inner environment of said inner cannula to said outer environment; and d) said inner cannula being positioned within said interior environment of said outer test tube so that said bottom end and an arm extension of said inner cannula are aligned with said lower faucet of said outer test tube, said top funnel opening fitting securely within said open top end of said outer test tube and said arm extension being aligned with said upper faucet of said outer test tube, to allow materials to be poured into said funnel opening of said cannula and pass through said arm extensions, bottom end and upper or lower faucets to said exterior environment of said outer test tube without being exposed to said interior environment of said outer test tube.

In a second embodiment of the instant invention, the stem of the inner cannula is off center of the funnel opening. While the funnel opening has the same diameter as the open top end of the test tube, the stem of the cannula is not centered inside the outer test tube.

In a third embodiment of the instant invention, the diameter of the funnel opening of the inner cannula is smaller than the open top end of the outer test tube. In this embodiment a beaker may be used in place of the outer test tube. In order to secure the inner cannula, the funnel opening or stem of the inner cannula may be attached to the sidewall of the beaker and/or the curved open bottom of the inner cannula may be attached to the closed bottom end of the beaker. Additionally, in this embodiment, as well as the two embodiments described above, an air vent may be manufactured as an additional arm off of the arm extension of the inner cannula. This Y-arm is an air vent that prevents the probe wash vessel from acting as a siphon. It should be noted that, where the inner cannula does not contain an air vent, the hoses which are connected to the arm extensions of the inner cannula will possess an air vent.

The instant invention maybe used in automated preparation stations and Autosampler systems for equipment including, but not limited to, Gas Chromatography systems (GC), Liquid Chromatography systems (LC), Atomic Absorption Spectroscopy systems (AA), Inductively Coupled Plasma Atomic Emission Spectroscopy systems (ICP), auto-analyzer systems, auto-titration systems, Ion Chromatography systems (IC), Total Organic Carbon analyzers (TOC), Ultra Violet Spectrometers systems (UV), automated metal digestion systems and automated dilution systems. Specific manufacturers of such equipment include, but are not limited to, Perkin Elmer (AS90 Autosampler), Thermo Jarrell Ash (TJA 300 Autosampler), Leeman Labs (AP200 II), Hewlett Packard, Varian, VG Elemental, Brinkman (Metrohm 730 Sample changer), Shimadzu, Sievers (TOC AS800), Leap Technologies and Dionex.

Referring more particularly to the drawings, wherein like numbers designate like parts throughout, FIG. 1, which will be more fully described herein-below, represents the invention, as assembled, in two dimensions. The probe wash vessel (1) comprises an outer test tube (2), an inner cannula (25) and at least two faucets (20).

Figure 2A:
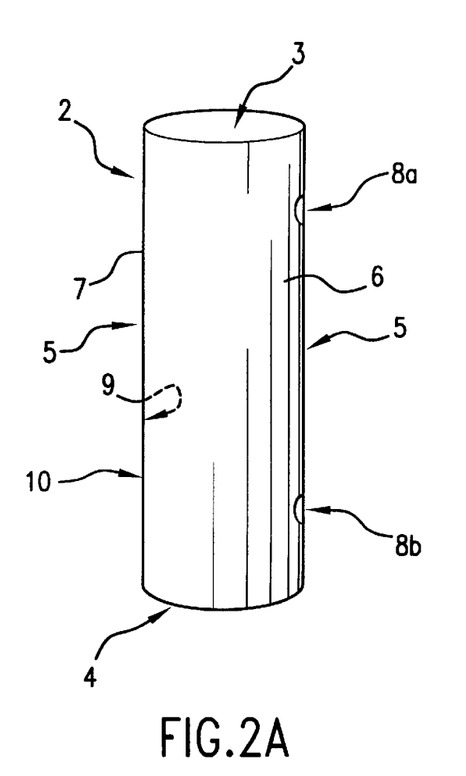
FIG. 2A and FIG. 2B are perspective views which depict two possible embodiments of the outer test tube.
Figure 2B:
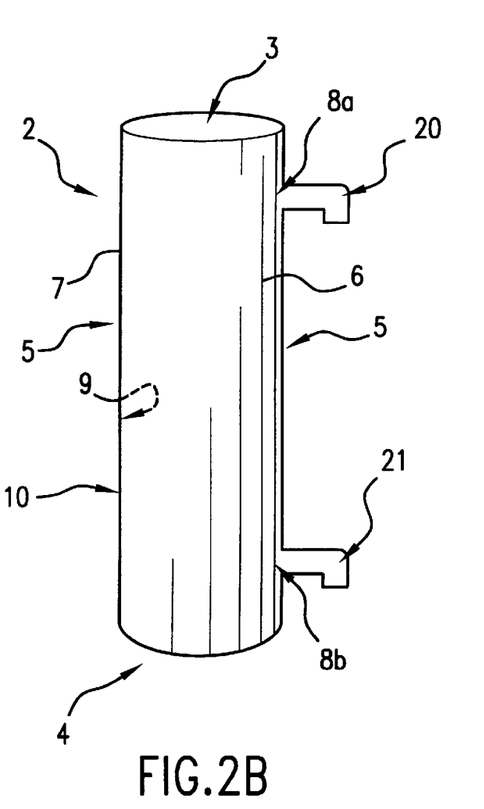

FIG. 2A and FIG. 2B depict two embodiments of the outer test tube (2) of the probe wash vessel (1). The outer test tube (2) has a first length and a first diameter and comprises an open top end (3), a closed bottom end (4) and a first cylindrical sidewall (5). The diameter of the outer test tube is about 10 mm to about 60 mm. Preferably, the outer test tube has a diameter of about 15 mm to about 40 mm. More preferably, the diameter of the outer test tube is about 20 mm to about 30 mm. The length of the outer test tube is about 5 cm to about 15 cm. Preferably, the length of the outer test tube is about 7 cm to about 12 cm. Most preferably, the outer test tube is about 8 cm to about 11 cm long.

The outer test tube (2) also possesses an interior environment (6) and an exterior environment (7). The first cylindrical sidewall (5) has an inner surface (9) and an outer surface (10). The outer test tube (2) may be made of any material that may be shaped into a test tube form. Types of such material include, but are not limited to teflon, glass, plastics and the like. The outer test tube (2) may have at least two holes (8a and 8b) in said first cylindrical sidewall (5), as shown in FIG. 2A.

Preferably, one hole (8a and 8b) is positioned closer to the closed bottom end (4) of the outer test tube, and one hole (8a and 8b) is positioned closer to the open top end (3) of the outer test tube. As depicted in FIG. 2B, the outer test tube (2) may also be made so that at least two faucets, an upper faucet (20) and a lower faucet (21), extend from the outer surface (10) of said cylindrical sidewall (5). Said faucets (20 and 21) are aligned with said holes (8a and 8b) of said first cylindrical sidewall (5) such that fluids may pass from the interior environment (6) of said outer test tube (2) through the faucets (20) to the exterior environment (7).

Figure 3:
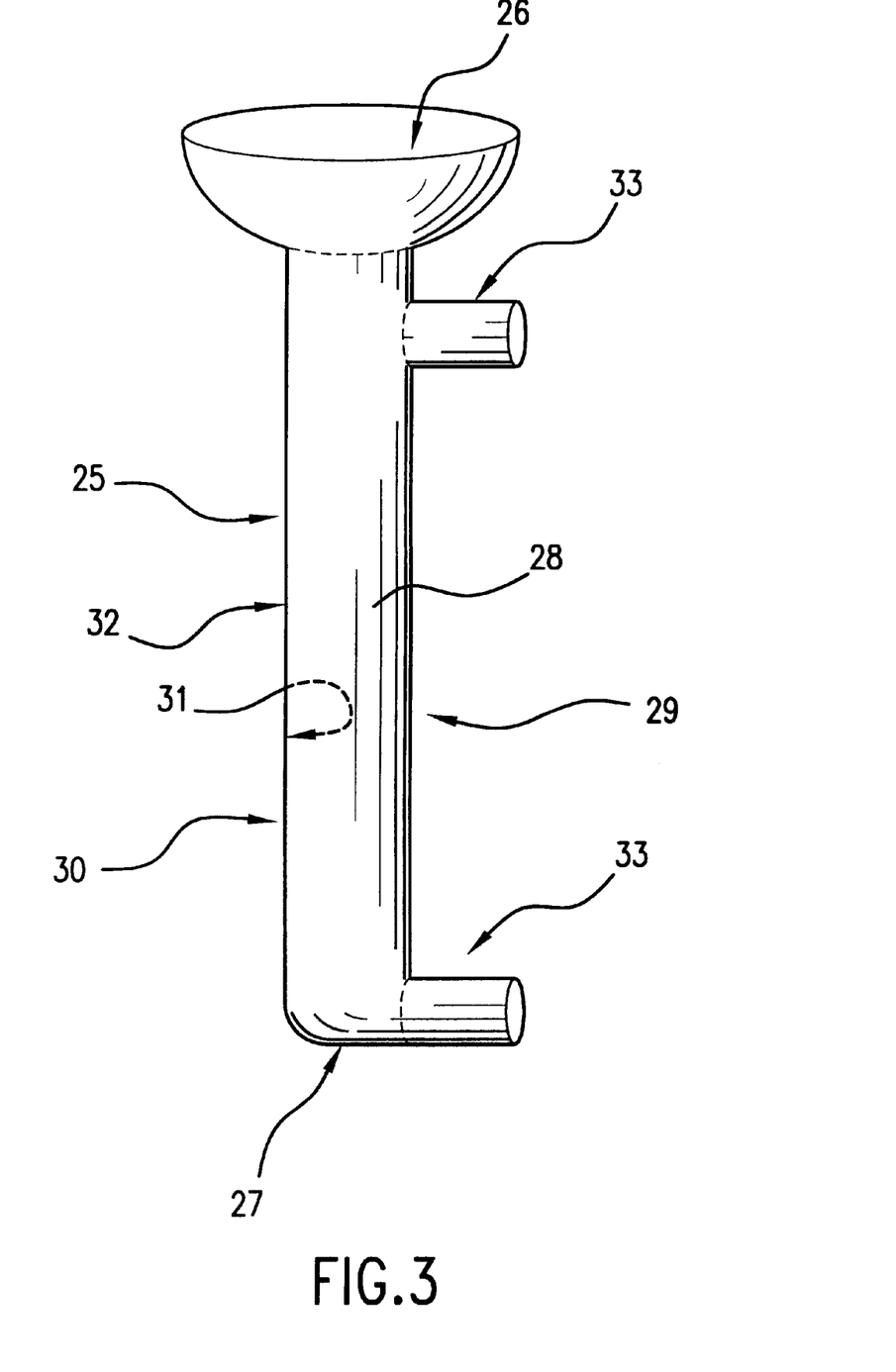
FIG. 3 is a perspective view of the inner cannula.

FIG. 3 depicts the inner cannula (25) of the probe wash vessel (1). Said inner cannula (25) has a second length which is shorter than said first length of the outer test tube (2). The length of the inner cannula is about 4 cm to about 14 cm. Preferably, the length of the inner cannula is about 6 cm to about 11 cm. More preferably, the inner cannula is about 7 cm to about 10 cm long. Said inner cannula (25) has a top funnel opening (26), which has a diameter that is about equal to said first diameter of the outer test tube (2), an open curved bottom end (27), an interior environment (28) and an exterior environment (29). The inner cannula (25) also has a stem (30), which comprises a second cylindrical sidewall (31), and has a second diameter which is smaller than said first diameter of the outer test tube (2). The diameter of the stem is about 2 mm to about 15 mm. Preferably, the diameter of the stem is about 4 mm to about 8 mm. Most preferably, the stem has a diameter of about 5 mm to about 6 mm. The stem (30) extends between the top funnel opening (26) and the open curved bottom end (27), and possesses an inner surface (31) and an outer surface (32). Arm extensions (33) may be added to the outer surface (10) of the outer test tube or they may be manufactured as part of the outer test tube (2). Regardless of the method used, at least two arm extensions (33) are attached to the outer surface of said stem (30) which protrude into the outer environment (29) of said inner cannula (25).

Figure 1:
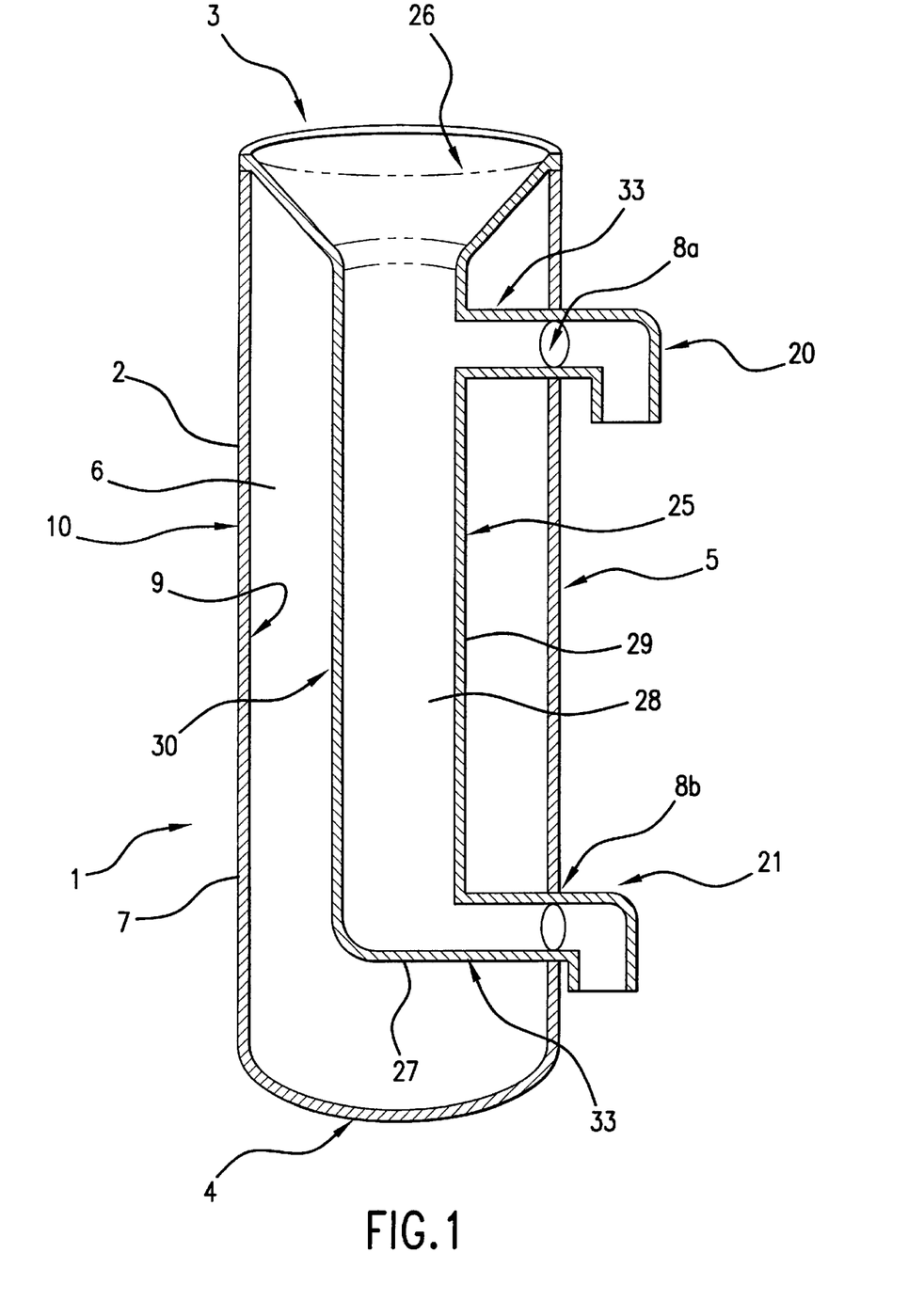
FIG. 1 is a view in perspective of the instant invention, as assembled.

As shown in FIG. 1, the inner cannula (25) is positioned within the interior environment (6) of the outer test tube so that the open curved bottom end (27) and an arm extension (33) of the inner cannula are aligned with one of the holes (8a and 8b) and the lower faucet (21) of the outer test tube.

Additionally, another arm extension (33) of the inner cannula is aligned with a second hole (8b) and the upper faucet (20) of the outer test tube. This placement also allows the top funnel opening (26) to fit securely in the open top end (3) of the outer test tube.

Figure 4:
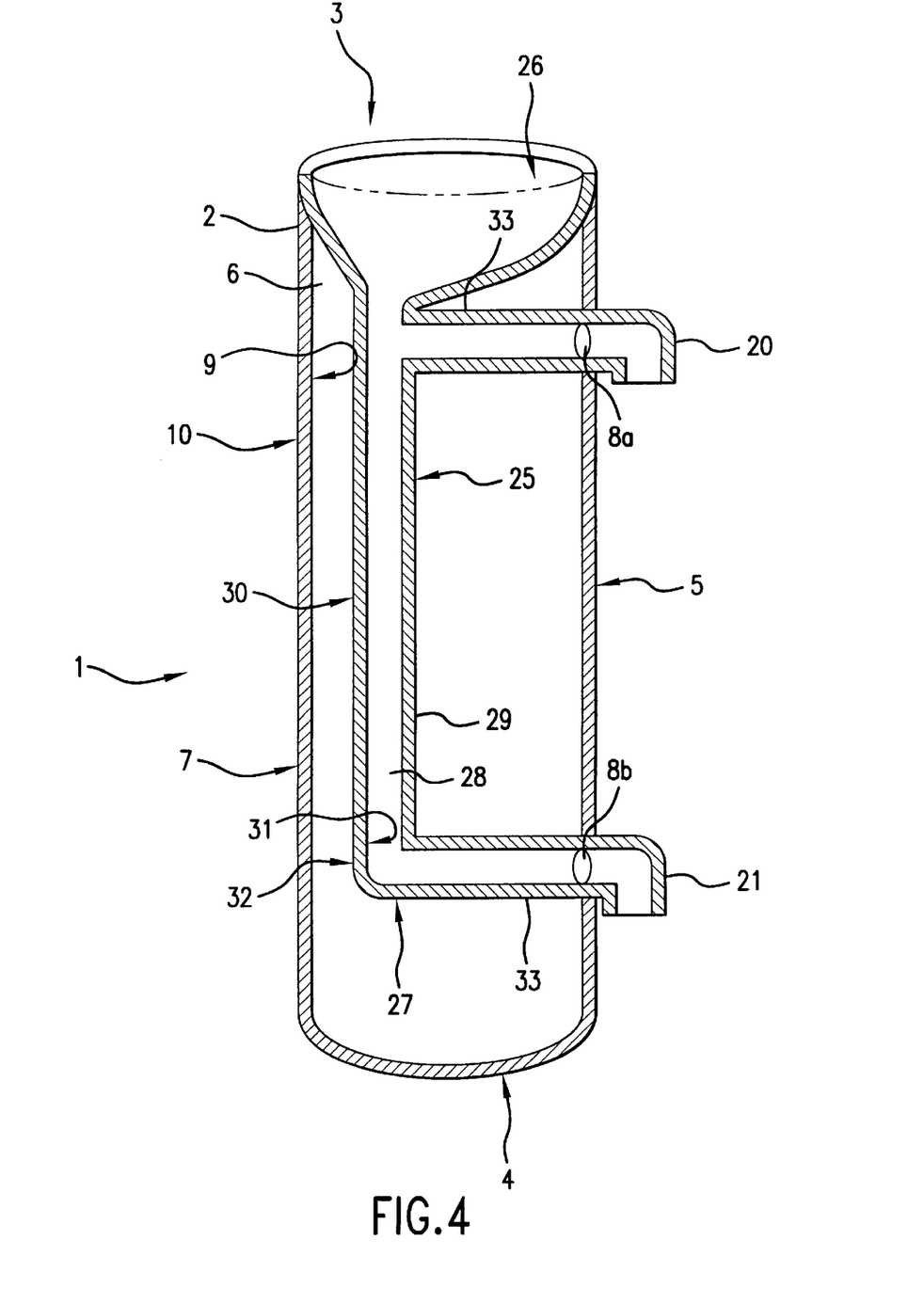
FIG. 4 is a perspective view of a second embodiment of the instant invention, as assembled.

Additionally, as depicted in FIG. 4, the instant invention may be assembled such that the stem (30) of the inner cannula is not centered within the open top end (3) of the outer test tube. Rather, the funnel opening (26) of the inner cannula may be positioned to sit within the open top end (3) of the outer test tube, but the stem (30) of the cannula is off-center.

Figure 5A:
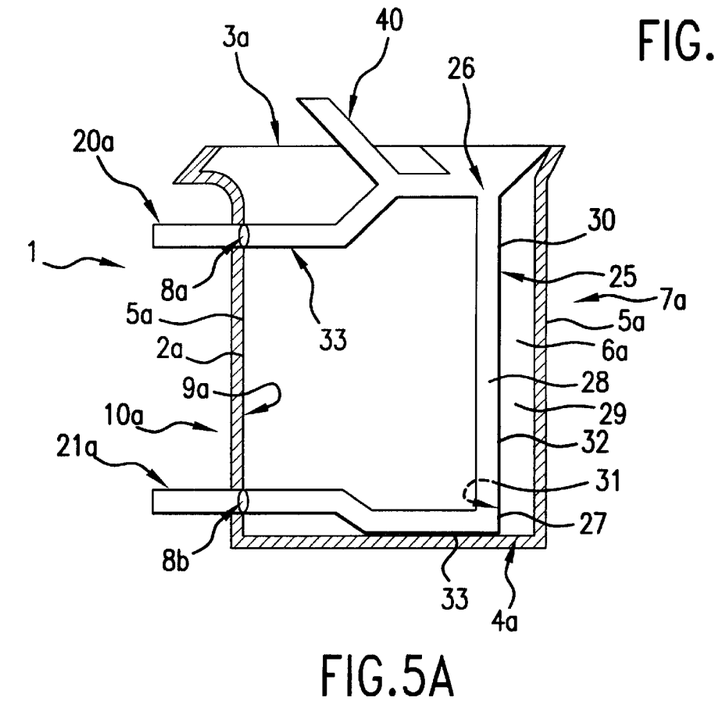
FIG. 5A is a perspective view of a third embodiment of the instant invention, as assembled.
Figure 5B:
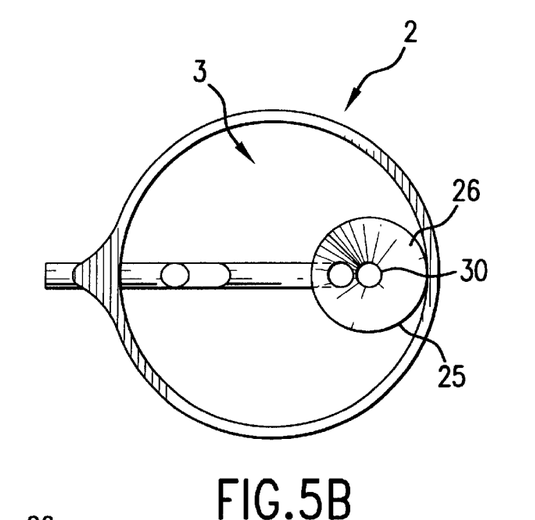
FIG. 5B is a top view of the third embodiment.

FIG. 5A and FIG. 5B depict a third embodiment of the invention where the top funnel opening (26) of the inner cannula has a diameter that is smaller than the diameter of the open top end (3a) of the outer test tube. In this embodiment, a beaker (2a) may be used as the outer test tube. The beaker (2a), like the outer test tube (2) depicted in FIG. 2A and FIG. 2B, has an open top end (3a), a closed bottom end (4a), an interior environment (6a), an exterior environment (7a), a first cylindrical sidewall (5a) and at least two holes (8a and 8b) in said first cylindrical sidewall (5a). Said first cylindrical sidewall (5a) also has an inner surface (9a) and an outer surface (10a). The beaker (2a) may also possess at least two faucets, an upper faucet (20a) and a lower faucet (21a), which are aligned with said holes (8a and 8b) and extend from the outer surface (10a) of said first cylindrical sidewall into the exterior environment (7a) of the beaker.

The elements of the inner cannula (25) depicted in FIG. 5A are identical in name and function to those depicted in FIG. 3 or FIG. 1, except that an air vent (40) has been added to the arm extension (33) that is positioned closest to the top open end (3a) of the beaker. This air vent (40) could be added to the inner cannula (25) or outer test tube (2) in any of the other embodiments or the hoses connected to the upper or lower faucets (20/21 or 20a/20a) may contain the air gap valve. The air vent (40) prevents the inner cannula from acting as a siphon and keeps the fluids flowing smoothly. FIG. 5B depicts a top view of the third embodiment and further illustrates that the top funnel opening (26) is smaller than the open top end (3). In the third embodiment, the diameter of the beaker is about 30 mm to about 150 mm. Preferably, the diameter of the beaker is about 40 mm to about 100 mm. More preferably, the diameter of the beaker is about 50 mm to about 70 mm. The length of the beaker is about 4 cm to about 20 cm. Preferably, the length of the beaker is about 7 cm to about 9 cm. The length of the inner cannula is about 3 cm to about 19 cm. Preferably, the inner cannula is about 6 cm to about 8 cm long. Additionally, the diameter of the stem of the inner cannula is about 2 mm to about 20 mm. Preferably, the diameter of the stem is about 3 mm to about 10 mm. More preferably, the diameter of the stem is about 4 mm to about 7 cm.

The embodiments depicted in FIGS. 4, 5A and 5B are useful when the automated equipment being utilized possesses a large holding apparatus which requires a container the size of a beaker or larger. There are certain machines that have been manufactured to use a large container, such as a bath wash, to clean the probe. For such machines, the probe wash vessel can be made such that the outer test tube fits in the holder for the bath wash while the inner cannula is positioned within the outer test tube to provide an efficient wash vessel that has a decreased volume capacity and reduces the wash time.

Figure 6:
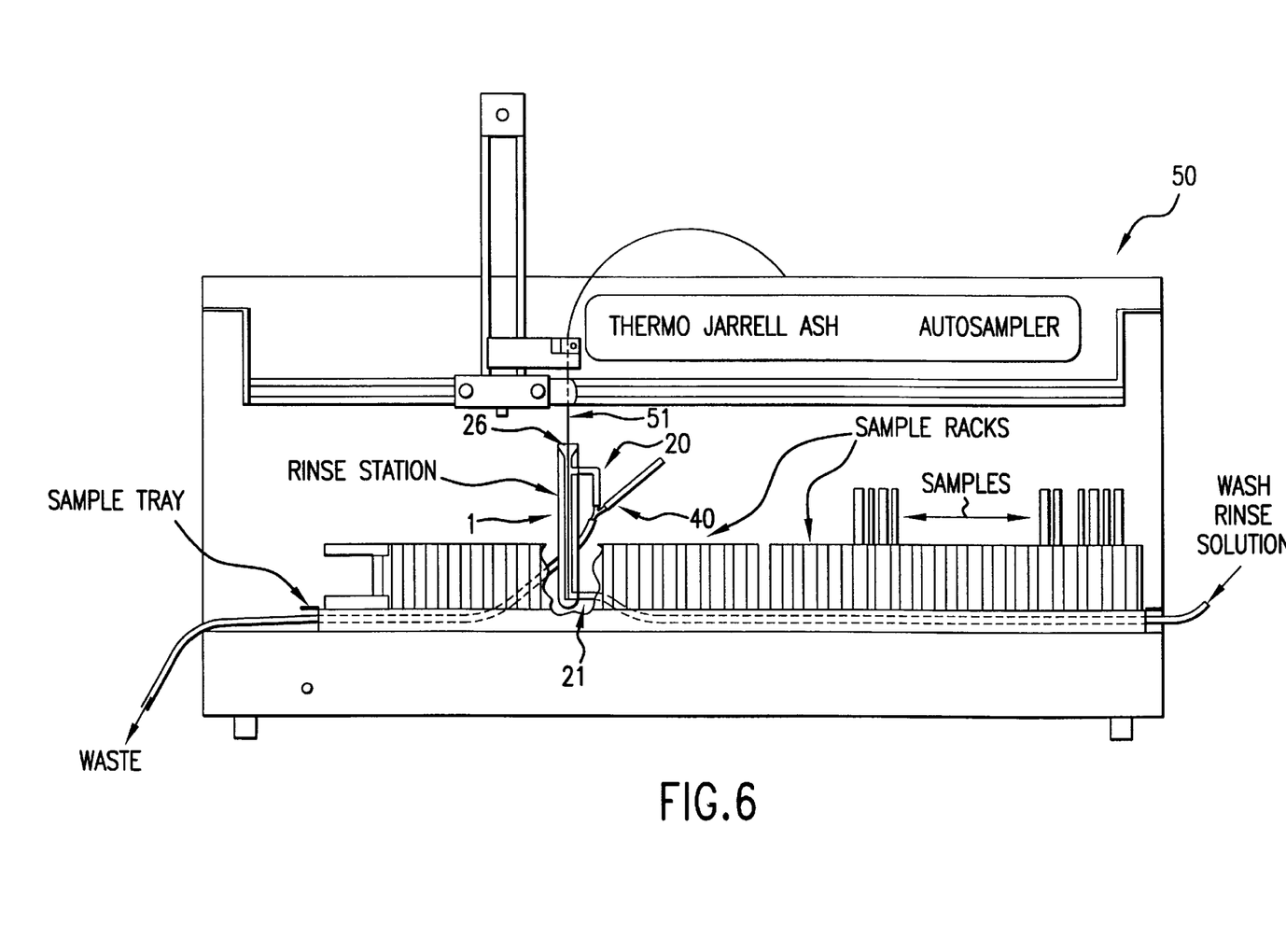
FIG. 6 is a perspective view of the instant invention in operation in an autosampler.

FIG. 6 demonstrates the probe wash vessel depicted in FIG. 1 in operation. The probe wash vessel (1) may be placed in the appropriate holder of an autosampler (50), or similar automated equipment. Tubing is connected to the upper (20) and lower (21) faucets of the probe wash vessel (1) and wash or rinse solvent is pumped through the lower faucet (21) to the interior environment (28) of the inner cannula. The wash solvent moves up the length of the inner cannula (25) and exits the inner cannula as waste through the upper faucet (20). Either the tubing connected to the upper faucet or the upper faucet (20) itself will possess an air vent (40) to prevent the probe wash vessel (1) from acting as a siphon. The probe (51) of the autosampler (50) enters the open top end (3) of the outer test tube and is guided down to the interior environment (28) of the inner cannula by the top funnel opening (26). Once the probe is in the interior environment (28) of the inner cannula, both the internal and external areas of the probe (51) are contacted with a concentrated stream of wash solvent.

The assembly of the inner cannula inside the outer test tube, as shown in FIG. 1, facilitates the washing of probes because of several distinct features. First, the outer test tube can be manufactured so that it can be utilized with most automated sampling equipment. Second, the inner cannula can be designed with a diameter that is most effective for the type of probe being used. The reduced size of the inner cannula allows for a more concentrated contact between the probes and the wash solvent, which ensures an improved wash. The reduced size also reduces the volume of solvent necessary to thoroughly wash the probes. Third, the funnel opening of the inner cannula guides the probe to the solvent so that it is unnecessary for an operator of the equipment to be present to ensure a precise entry of the probe into the vessel.

In this disclosure, there is shown and described only the preferred embodiment of the invention, but it is to be understood that the invention is capable of changes or modifications within the scope of the inventive concept as expressed herein.

What is claimed is:

1. A probe wash vessel comprising
   a) an outer test tube of a first length, having an open top end of a first diameter, a closed bottom end, a first cylindrical sidewall, an interior environment and an exterior environment, said first cylindrical sidewall having an inner surface and an outer surface, which extend between said open top end and said closed bottom end, and at least two holes in said first cylindrical sidewall;
   b) at least two faucets, which are aligned with said holes of said outer test tube and attached to the outer surface of said first cylindrical sidewall, a lower faucet being positioned closer to said closed bottom end of said outer test tube and an upper faucet being positioned closer to said open top end of said outer test tube;
   c) an inner cannula of a second length which is shorter than said first length, said inner cannula having a top funnel opening, a bottom end, an inner environment, an outer environment and a stem, which comprises a second cylindrical sidewall extending between said top funnel opening and said bottom end, said stem having an outer surface, an inner surface and a second diameter that is smaller than said first diameter, said stem having at least two arm extensions, upper and lower arm extensions, protruding from the outer surface of said stem to allow materials to pass from said inner environment of said inner cannula to said outer environment; and
   d) said inner cannula being positioned within said interior environment of said outer test tube so that said bottom end and lower arm extension of said inner cannula are aligned with said lower faucet of said outer test tube, said top funnel opening fitting securely within said open top end of said outer test tube and said upper arm extension being aligned with said upper faucet of said outer test tube to allow materials to be poured into said funnel opening of said cannula and pass through said upper and lower arm extensions, bottom end and upper or lower faucets to said exterior environment of said outer test tube without being exposed to said interior environment of said outer test tube.

2. The probe wash vessel of claim 1, wherein the probe wash vessel is made from teflon, glass or plastic.

3. The probe wash vessel of claim 1, wherein the diameter of the outer test tube is about 10 mm to about 60 mm and the diameter of the stem is about 2 mm to about 15 mm.

4. The probe wash vessel of claim 3, wherein the diameter of the outer test tube is about 20 mm to about 30 mm and the stem has a diameter of about 5 mm to about 6 mm.

5. The probe wash vessel of claim 1, wherein the length of the outer test tube is about 5 cm to about 15 cm and the length of the inner cannula is about 4 cm to about 14 cm.

6. The probe wash vessel of claim 5, wherein the outer test tube is about 8 cm to about 11 cm long and the inner cannula is about 7 cm to about 10 cm long.

7. The probe wash vessel of claim 1, wherein the top funnel opening of the inner cannula is off-center relative to the outer test tubed.

8. The probe wash vessel of claim 1, wherein the outer test tube is a beaker.

9. The probe wash vessel of claim 8, wherein the top funnel opening of the inner cannula has a diameter of about 2 mm to about 20 mm and the open top end of the beaker has a diameter of about 30 mm to about 150 mm.

10. The probe wash vessel of claim 9, wherein the top funnel opening of the inner cannula has a diameter of about 4 mm to about 7 mm and the open top end of the beaker has a diameter of about 40 mm to about 60 mm.

11. The probe wash vessel of claim 8, wherein the beaker is about 4 cm to about 20 cm in length and the inner cannula is about 3 cm to about 19 cm longs.

12. The probe wash vessel of claim 11, wherein the beaker is about 7 cm to about 9 cm in length and the inner cannula is about 6 cm to about 8 cm long.

* * * * *